United States Patent [19]
Adams

[11] Patent Number: 5,338,304
[45] Date of Patent: Aug. 16, 1994

[54] NEEDLE PROTECTED SYRINGE

[75] Inventor: Robert D. Adams, Hainesport, N.J.

[73] Assignee: Adventec, Inc., Camden, N.J.

[21] Appl. No.: 121,049

[22] Filed: Sep. 14, 1993

Related U.S. Application Data

[63] Continuation of Ser. No. 898,796, Jun. 15, 1992, abandoned.

[51] Int. Cl.$^5$ .............................................. A61M 5/00
[52] U.S. Cl. ...................................... 604/110; 604/195
[58] Field of Search ............... 604/110, 195, 187, 192, 604/218, 263

[56] References Cited

U.S. PATENT DOCUMENTS

| | | | |
|---|---|---|---|
| 4,507,117 | 6/1988 | Vining et al. | 604/196 |
| 4,978,343 | 12/1990 | Dysarz et al. | 604/195 |
| 4,985,021 | 1/1991 | Straw et al. | 604/198 |
| 5,112,316 | 5/1992 | Venturini | 604/195 |
| 5,122,118 | 6/1992 | Haber et al. | 604/110 |
| 5,125,898 | 6/1992 | Kaufhold, Jr. et al. | 604/195 X |
| 5,147,303 | 9/1992 | Martin | 604/110 |
| 5,152,750 | 10/1992 | Haining | 604/195 |
| 5,171,300 | 12/1992 | Blake, III et al. | 604/110 |
| 5,176,640 | 1/1993 | Nacci et al. | 604/110 |
| 5,180,369 | 1/1993 | Dysarz | 604/110 |
| 5,180,370 | 1/1993 | Gillespie | 604/110 |
| 5,188,597 | 2/1993 | Sweeney et al. | 604/110 |
| 5,190,526 | 3/1993 | Murray et al. | 604/110 |
| 5,195,985 | 3/1993 | Hall | 604/195 |
| 5,205,824 | 4/1993 | Mazur | 604/110 |
| 5,211,628 | 5/1993 | Marshall | 604/110 |
| 5,256,151 | 10/1993 | Chul | 604/195 |
| 5,263,934 | 11/1993 | Haak | 604/110 |

FOREIGN PATENT DOCUMENTS

| | | |
|---|---|---|
| 0347742 | 2/1989 | European Pat. Off. |
| 0405039 | 1/1991 | European Pat. Off. |
| 0438368 | 7/1991 | European Pat. Off. |
| 0480862 | 4/1992 | European Pat. Off. |
| 9114465 | 10/1991 | PCT Int'l Appl. |

*Primary Examiner*—John D. Yasko
*Attorney, Agent, or Firm*—Volpe and Koenig

[57] ABSTRACT

An improved syringe of the type having a hollow body which is closed at one end by an injection means and is open at the other end, the open end receives an elongated plunger means which moves through the hollow body and forces the contents of the body through the injection means. The improvement is comprised of a resilient compressive member which retracts the injection means into a protective covering.

18 Claims, 8 Drawing Sheets

NEEDLE PROTECTED SYRINGE

This is a continuation of application No. 07/898,796, filed on Jun. 15, 1992, now abandoned.

BACKGROUND OF THE INVENTION

1. Field of the Invention

The present invention relates generally to protection against accidental injection from a needle. More particularly, the present invention relates to the protection from accidental injection from a used needle of the type commonly associated with medical practice. Most particularly, the present invention relates to protection against accidental injection from a used, single dose syringe of the type common in medical practice.

2. Description of the Prior Art

The art has recognized, for some time, the desirability of protecting personnel from accidental injection. More recently, concerns have been expressed about the possibility of transmitting serious or potentially fatal infection through accidental injection with a used syringe needle. Most recently, the Occupation Safety and Health Administration has issued guidelines which are generally known as Standard 1910.1030.

As stated previously, the art has recognized the desirability of protecting against accidental injection. However, it is believed that suitable protective devices are not available.

It is an object of the present invention to provide protection which does not require exposure to the used needle.

SUMMARY OF THE INVENTION

In keeping with the effort to provide improved protection against accidental needle punctures, the improvement comprises a resilient, compressive member which retracts the needle into a protective cover. The needle is retracted into the protective cover for a distance which is at least equal to the length of the needle. In the preferred embodiments, the entire length of the needle is contained within the protective cover.

DESCRIPTION OF THE PREFERRED EMBODIMENTS

The preferred embodiments will be described with reference to the attached drawing figures. Like elements are identified by the same numeral throughout.

Figures 1, 2:
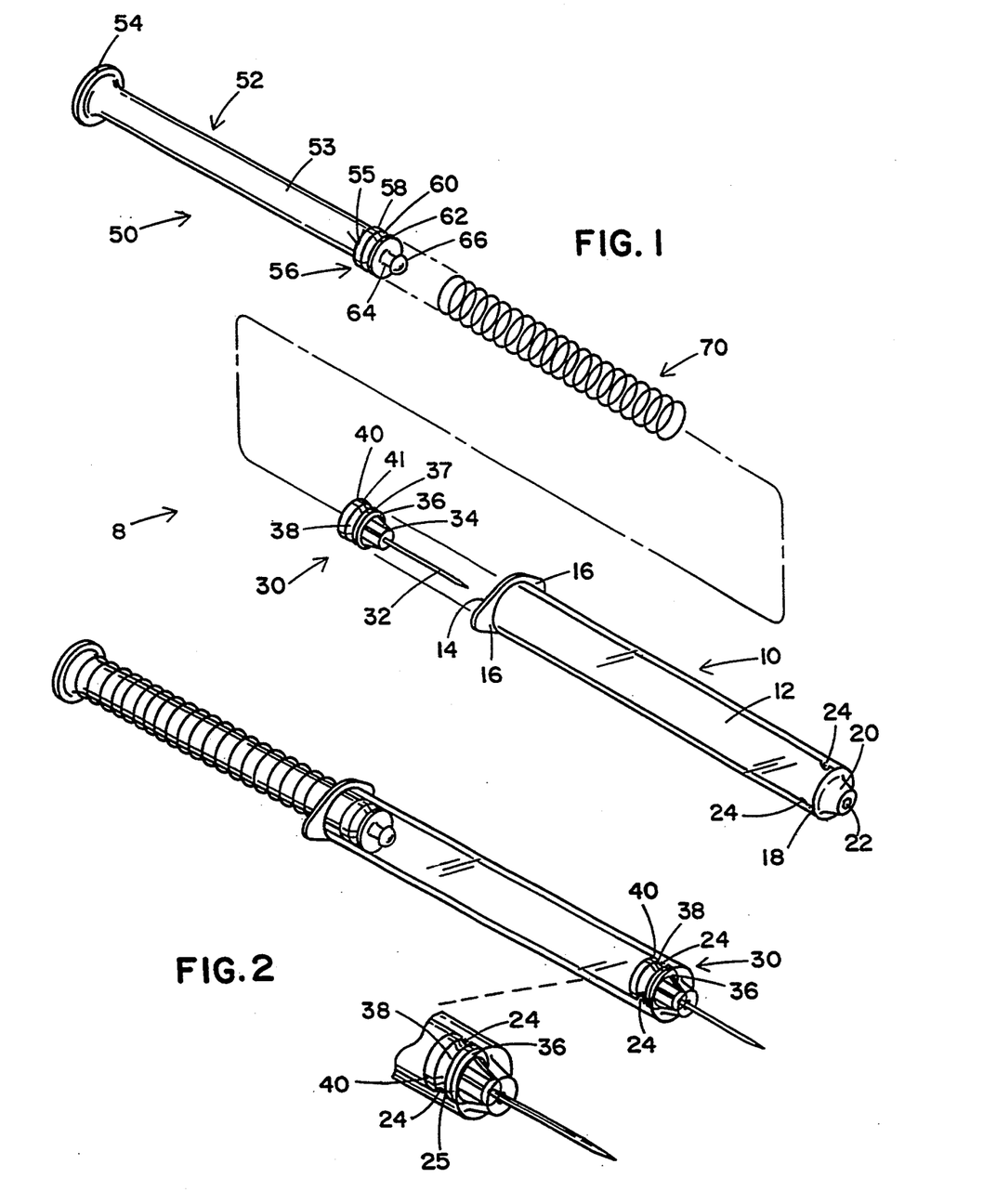
FIG. 1 is an exploded view of a syringe assembly in accordance with the present invention.
FIG. 2 depicts the syringe of FIG. 1 in an assembled but unused condition; the needle end of the syringe is shown in exploded form to more clearly depict the details thereof.
Figure 3:
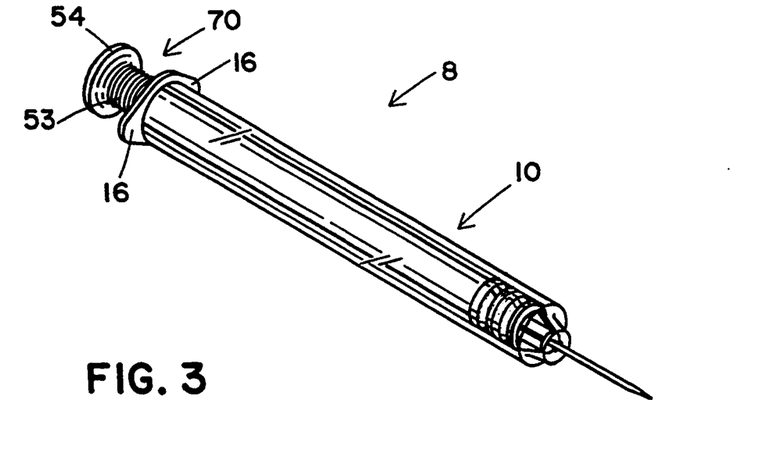
FIG. 3 depicts the syringe of FIG. 2 immediately after use.
Figure 4:
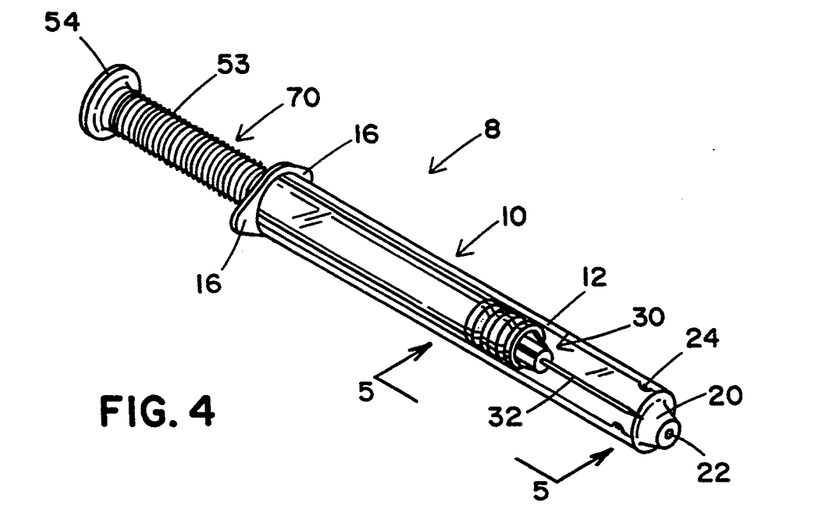
FIG. 4 depicts the syringe of FIG. 3 after it has been used and the needle has been retracted.

With reference to FIG. 1, there is illustrated one preferred embodiment 8 of the invention. This embodiment is comprised generally of the syringe 10, the needle assembly 30, the compressible member or spring 70, and the plunger member 50 which includes the sealing member 56.

The syringe 10 is comprised of a body portion 12 which has an open end 14 that is surrounded by finger grips 16. The body 12 is closed at the other end 18 by a truncated cone 20 which includes a central aperture 22 on the truncating plane of cone 20. On the interior of the hollow body 12 at a position adjacent to the closed end 18 are the projections 24, see FIG. 2. Presently it is preferred to use two opposed projections 24, however, one or more projections 24 may be used. Each projection 24 is provided with a flattened portion 25. Alternatively, the projections 24 may be replaced by an internal ring. It is the purpose of the projections 24 to retain the needle assembly 30 in position during insertion of the needle into the patient. As will be explained hereinafter, the critical criteria for such a holding member is that it resists the displacement force asserted against the needle assembly 30 during insertion into the patient.

Figure 7:
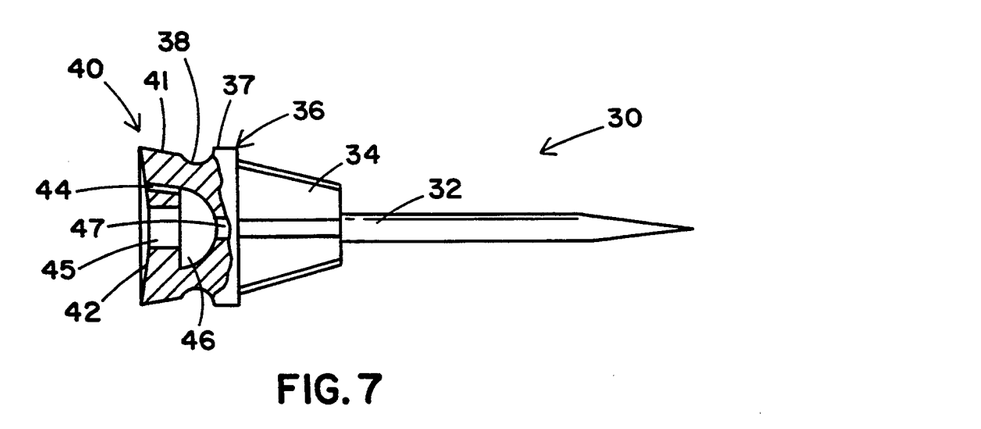
FIG. 7 is a side elevation, with a partial section, of the needle assembly depicted in the prior figures.

The needle assembly 30 is comprised of a needle 32 which is centrally positioned in the conical projection 34. The conical projection 34 compliments the interior of the truncated cone 20 in the syringe 10. Immediately adjacent to the projection 34 is a resilient collar 36. Immediately behind the collar 36 is the angular recess 38. Adjacent to the recess 38 is the sealing ring 40. The resilient collar 36, the angular recess 38 and the sealing ring 40 are all formed as a unitary molding of synthetic rubber. The needle assembly 30 includes an interior recess which communicates with the hollow needle 32. This structure will be described in more detail hereinafter with reference to FIG. 7. With reference to FIGS. 1, 2 and 7, the collar 36 generally compliments the interior diameter of the body 12 and is further dimensioned to fit in between the closed end 18 and the projections 24. As a result, the projections 24 will be disposed in the angular recess 38. The sealing ring 40 is dimensioned to establish a liquid tight seal against the interior of the body 12. The sides 41 of sealing ring 40 taper toward the recess 38 and the flattened portions 25 will abut collar 36. The trailing edge 37 of the collar 36 must provides the resistance against the retaining members 24 which prevents dislodgment of the needle assembly 30 during insertion into the patient. The flattened portion 25 will abut the edge 37 without regard to the fact that recess 38 is arcuate.

The compressive member 70 is a stainless steel coil spring. For a one cc syringe, it has been determined that the compressive member should be selected to require a compressive force of about four pounds to collapse it completely. The spring 70 has an interior diameter which permits the spring to override the shaft 52 of the plunger assembly 50 and to abut the force application pad 54. The compressive member 70, at least in that portion adjacent the open end 14 has a diameter which is larger than the open end 14. As will be understood by those skilled in the art, this results in the compressive member 70 being retained between its abutment with the syringe body defining the open end 14 and its abutment against the pad 54.

Figure 5:
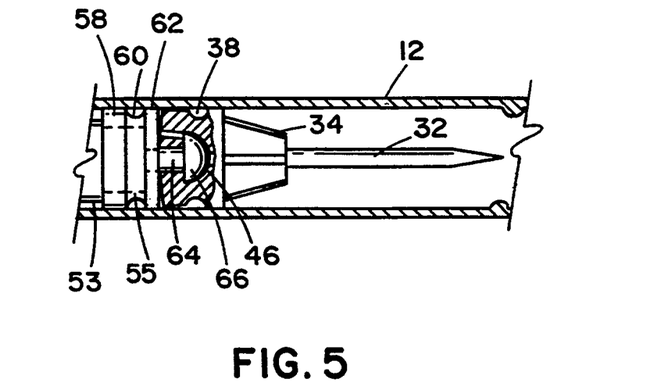
FIG. 5 is taken in the direction of the arrows 5—5 on FIG. 4 and includes a partial section in order to more fully depict the interconnection between the plunger assembly and the needle assembly.

The plunger assembly 50 includes a plunger portion 52 and a sealing member 56. Plunger member 52 has a shaft 53 which terminates at one end in the force application pad 54 and at the other end in a shouldered column 55 around which the sealing member 56 is seated. The shaft 64 depends from the column 55 and extends beyond the sealing member 56 for a short distance before it terminates in the hemisphere 66. This structure will be described in further detail hereinafter with reference to FIG. 5. The sealing member 56 includes an internal recess which generally surrounds the column 55 so that the ring 58 is seated against the shaft 53. The sealing member 56 has an angular recess positioned directly adjacent to the ring 58. Directly adjacent to the angular recess 60 is a sealing ring 62. Sealing ring 62 is dimensioned to establish a liquid tight seal against the interior of the syringe body 12 in the same manner as is known in the art.

In the preferred embodiment, ring 58 is also a liquid tight seal. However, ring 58 is provided primarily for the purpose of positioning the plunger assembly and does not require the liquid seal characteristics of sealing ring 62. While it is understood that ring 58, recess 60 and sealing ring 62 may be combined in a uniform sealing member, the present configuration is preferred since it permits the sealing ring 62 to act as a wiping member due to the recess 60 and the ring 58 provides guidance for the plunger. It should be noted at this point, that the plunger assembly 50 is maintained within the syringe body 12 due to the interference fit between the sealing member 62 and the interior of the body 12.

Figure 6:
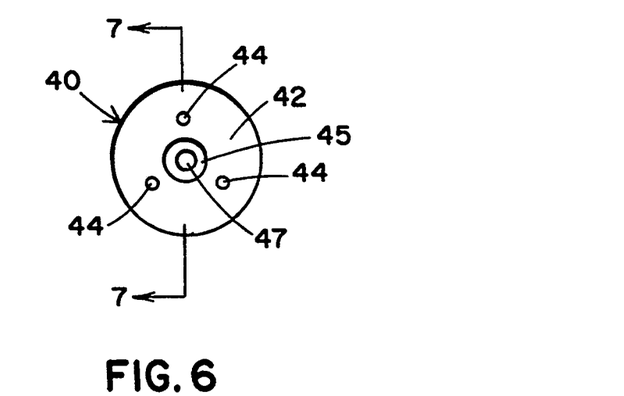
FIG. 6 is a top plan view of the needle assembly.

With reference to FIGS. 6 and 7 there is shown, respectively, a top plan view and a side view with partial section of needle assembly 30. With reference to FIG. 6, the area 42 within the sealing ring 40 is conical and funnels toward the central aperture 45. Spaced about the central aperture 45 are a plurality of tubes 44. With reference to FIG. 7, it can be seen that the central aperture 45 and the tubes 44 open into the common cavity or reservoir 46. The cavity or reservoir 46 is drained through tube 47 into the needle 32. The cavity 46 is sized to be slightly larger than the hemisphere 66. The aperture 45 has a diameter which is slightly larger than shaft 64; however, aperture 45 must be less than the diameter of hemisphere 66. The conical surface 42, tubes 44 and tube 47 pass the fluid into the needle 32 for injection. The tubes 44 also allow for some deflection as the hemisphere 66 is urged toward the reservoir 46. While the preferred embodiment is shown with three tubes 44, it will be understood that more and/or larger tubes may be utilized. It is expected that more tubes will be used with larger volumes. Likewise, an increased number of tubes will create a greater area of flexibility to assist in the insertion of the hemisphere 66.

Figure 8:
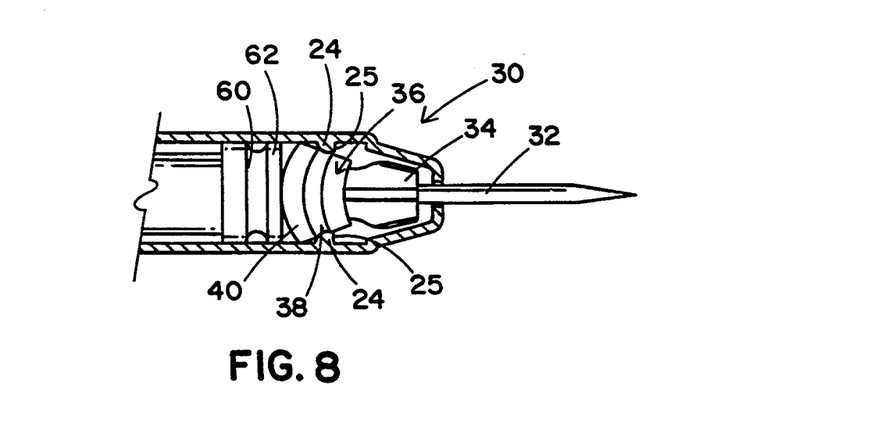
FIG. 8 illustrates the needle assembly as it is drawn into the syringe body.

With reference to FIG. 8, the withdraw of the plunger 50 causes the deformation of the needle assembly so that the collar 36 is released from the projections 24. Due to the arcuate recess 38 the assembly will neckdown to pass beyond the projections 24. Thereafter, the entire assembly will move freely with the plunger.

A second embodiment will be described with references to FIGS. 9 through 12. Like the prior embodiment, this embodiment utilizes a compress ire member to retract the needle into a protective cover. By way of distinction, the prior embodiment contemplated a syringe construction which was specifically designed to take advantage of the present invention within the traditional configuration of a syringe; whereas, the present embodiment is intended to be useful with the standard commercial syringes that are presently available in the market place.

Figure 9:
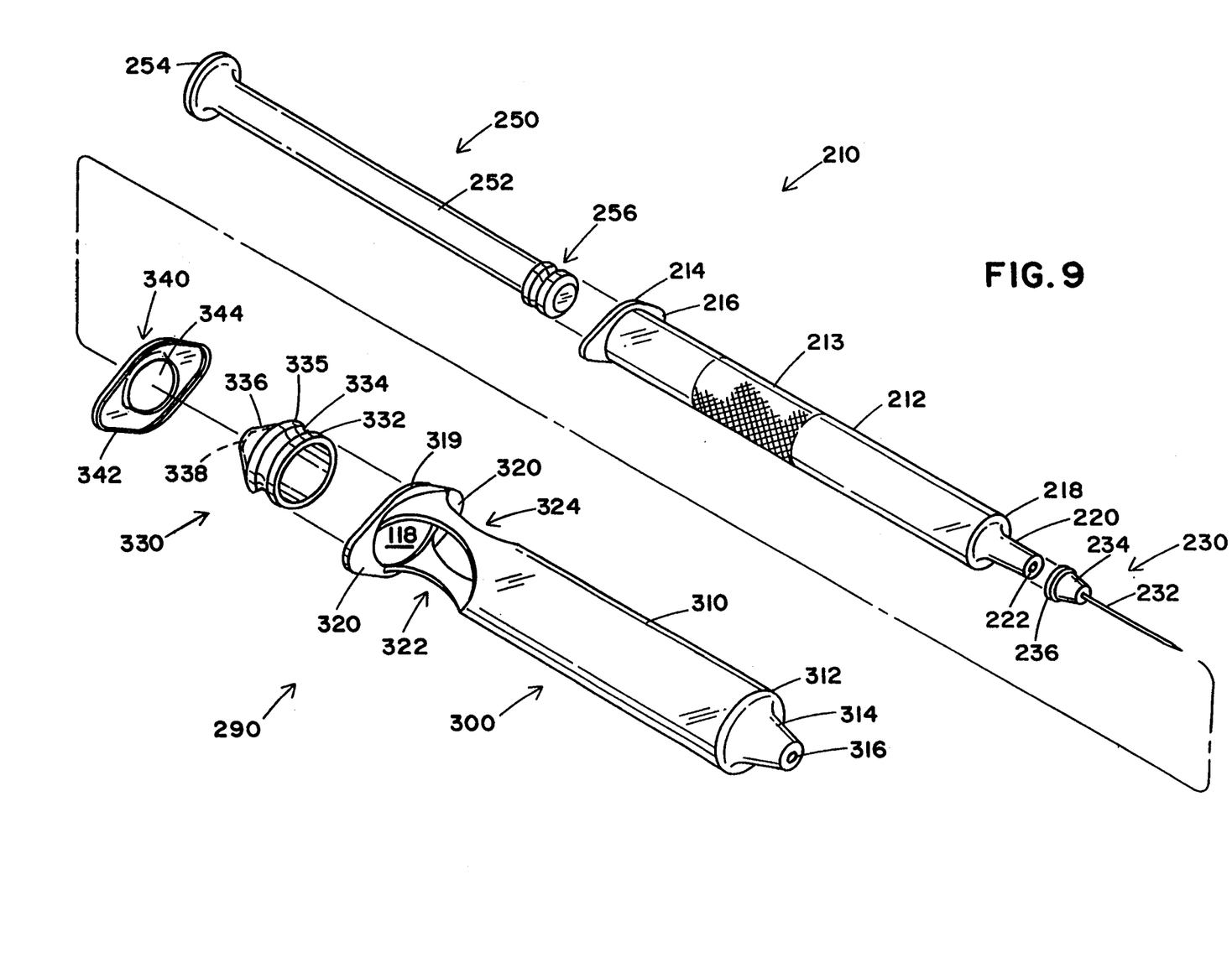
FIG. 9 is an exploded view of the syringe assembly in accordance with the present invention.

With reference to FIG. 9, there is shown a syringe 210 which is generally comprised of a syringe body 212, a needle assembly 230 and a plunger assembly 250. The assembled syringe is combined with a protective housing 290 which is comprised of a body member 300, a compressive member 330 and a cap 340.

Still with reference to FIG. 9, the syringe 210 is essentially the commercially available syringe with the single modification that an etched portion 213 has been added to the body 212 of the syringe. As in the past, the syringe has an open end 214 which is surrounded by finger grips 216. The other end of the syringe 212 is closed at base 218 with a projection 220 which extends from the base 218 and terminates in the aperture 222. The needle assembly 230 includes a needle 232, a conical portion 234 and a collar 236. As is known in the art, the needle assembly 230 is pressed onto the projection 220 so that projection 220 is inserted into the interior of cone 234 and the aperture 222 is in communication with the needle 232. The plunger assembly 250 is comprised of a plunger shaft 252, a finger application pad 254 and a sealing assembly 256.

With respect to the protective cover 290, the essential elements of the cover are the body 300 and the compressive member 330. Referring first to the body 300, it is generally configured like the syringe body 212. It includes a body portion 310 which has an interior dimension that is larger than the exterior of the body 212. The base end 312 of body 310 is closed and reduced in size to form the projection 314 which defines the aperture 316. The other end of the body 310 defines the apertures 318 which is surrounded by the collar 319 which defines the pads 320. Directly below the pads 320, the body 310 has two arcuate reliefs 322 and 324 which will be explained in more detail hereinafter. The resilient compressive member 330 is dimensioned to fit through the aperture 318 and into the body 310. The exterior diameter of the compressive resilient member 330 is substantially equal to the interior diameter of the body 310. The compressive member 330 has a lower ring portion 332, an intermediate or central relief portion 334 and a second ring 335. Extending from the second ring 335 is the conical portion 336 which defines therein a central aperture 338. As a result of this structure, the compressive resilient member will fold in accordion like fashion. The closure 340 has a dependent collar 342 which snaps about the collar 319. The closure 340 includes a central aperture 344 which is dimensioned to permit the syringe body to pass through the closure and into the protective cover 300.

Figure 10:
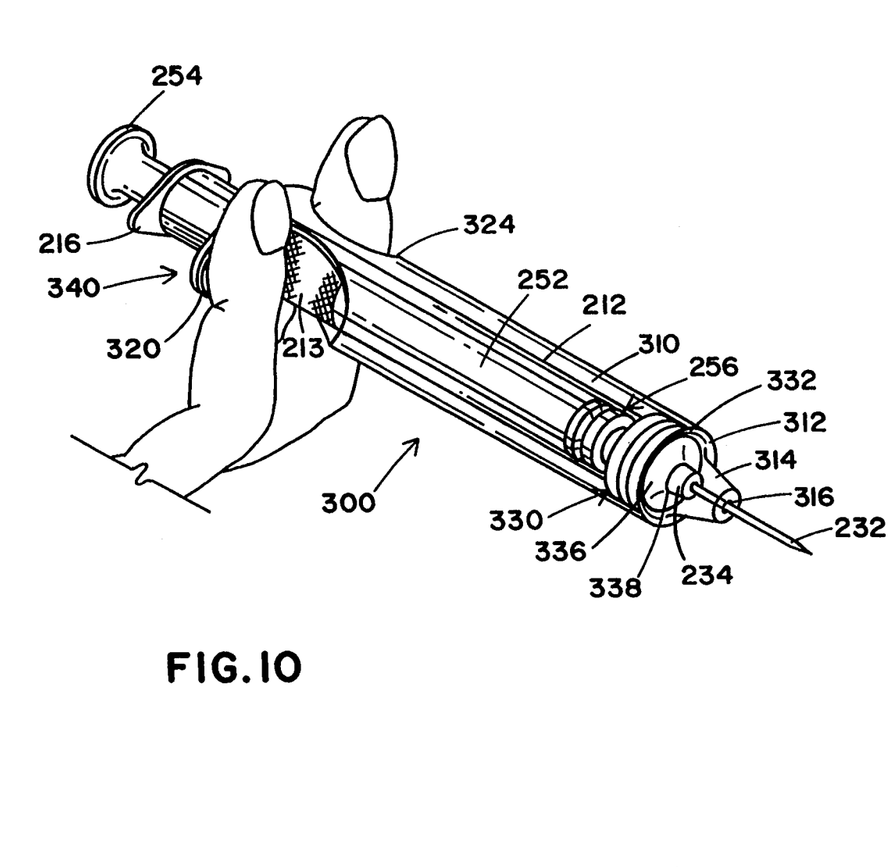
FIG. 10 depicts the syringe of FIG. 9 immediately after use.

Referring now to FIG. 10, the device of FIG. 9 is shown in its assembled form with the plunger 252 fully inserted. This approximates the condition of the device immediately after use. As can be seen from FIGS. 9 and 10, the compress ire resilient member 330 has collapsed upon itself in the manner of bellows as a result of the ring 332 abutting the end 312 of the protective cover 310. The cone 234 of needle assembly 230 is partially inserted into the aperture 338. The needle 232 extends through the aperture 316 by a sufficient distance to permit the necessary injection. At this time, it should be noted that the user's fingers are in contact with the etched portion 213 of the syringe body 212. This contact is facilitated by the arcuate release 322 and 324 in the protective cover 300. It will also be noted that the user's fingers are in contact with the pads 320 in a manner which is similar to the typical contact expected with the use of an unprotected syringe. The cover 34 0 provides a means for stabilizing the syringe within the protective cover 300. As will be understood by those skilled in the art, it is preferable to provide an aperture 344 which closely approximates the maximum diameter of the syringe to be inserted into the protective cover 300. This will aid in stabilizing the syringe. Likewise, the provision of an etched portion 213 is optional. It is believed that the etched portion 213 increases stability and the user's feel for the syringe.

Figure 11:
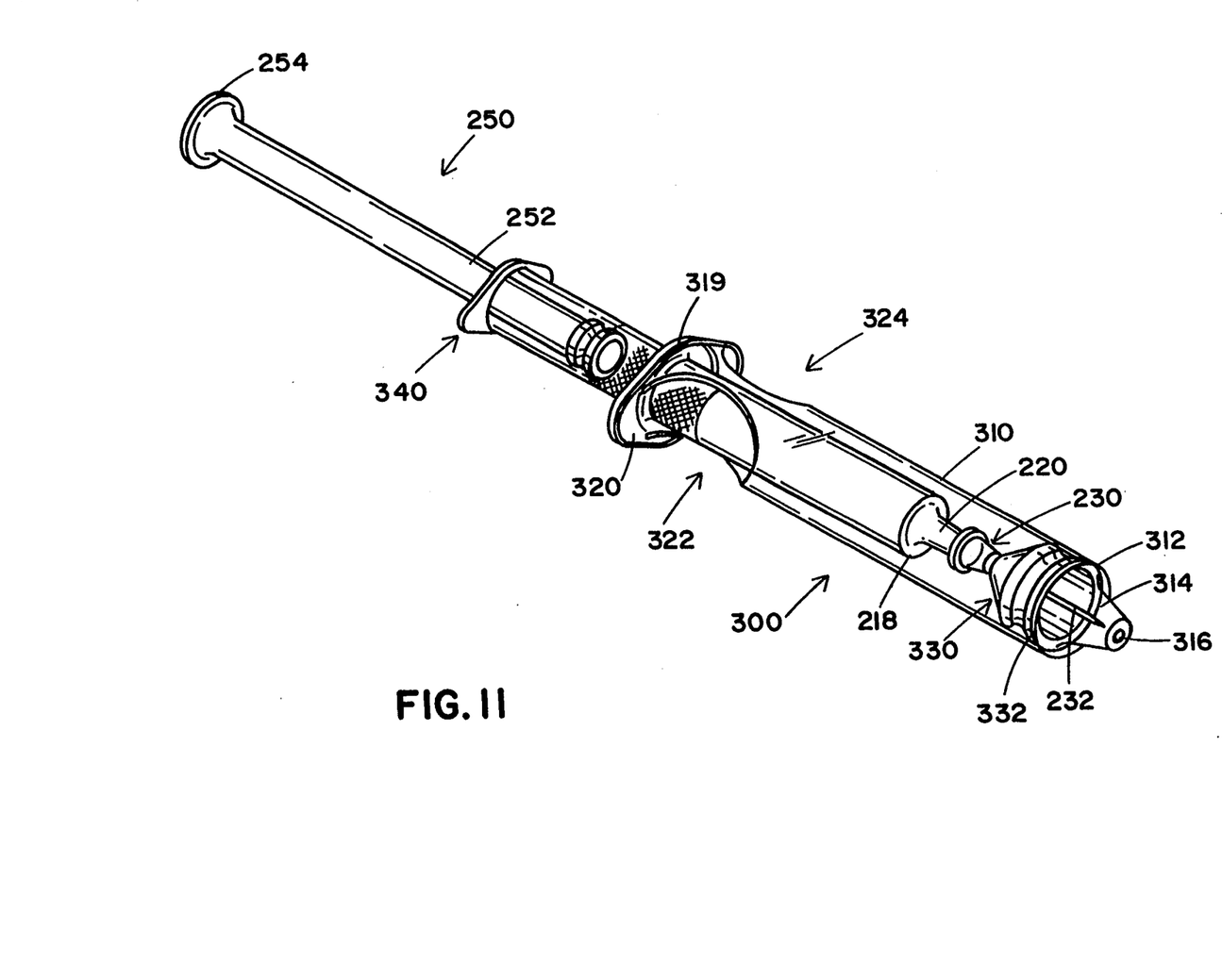
FIG. 11 depicts the syringe of FIG. 10 after the needle has been retracted.

With reference now to FIG. 11, the syringe is illustrated after use and after retraction of the injection means into the protective housing. As can be seen from FIG. 11, the compressive member 330 has rebounded to its original configuration. As a result, the force applied to the conical portion 234 of the needle assembly 230 has caused the needle to be retracted into the protective cover and beyond the aperture 316. As a result of the contact between the cone 336, as it defines the aperture 338, and the conical portion 234 of the needle assembly 230, the needle is retained within the protective housing. In this condition, the needle may be disposed of in the usual manner without exposing medical personnel to contact with the used needle.

Figure 12:
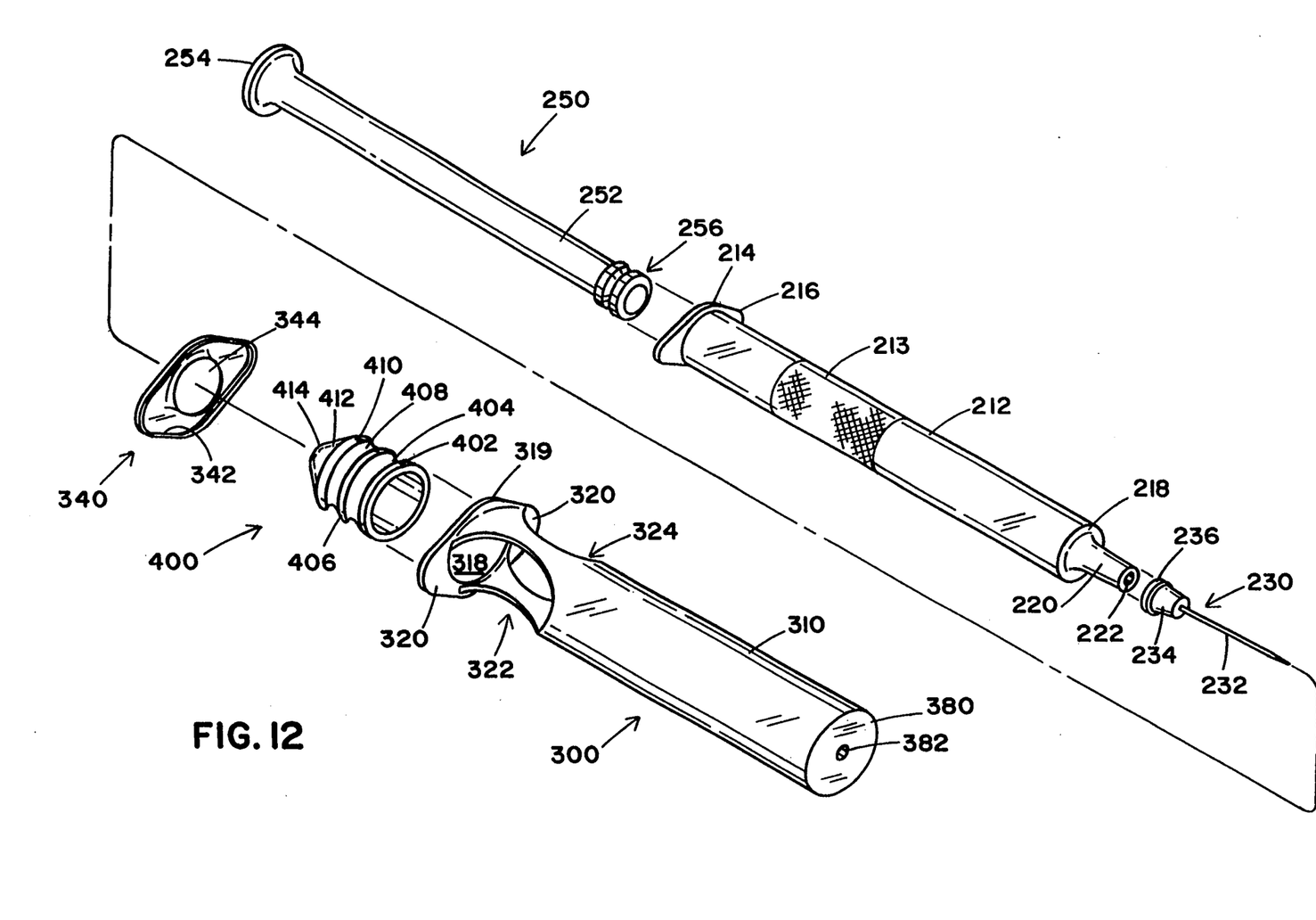
FIG. 12 depicts an alternative embodiment for the protective cover of the assembly shown in FIG. 9.

With reference to FIG. 12, there is shown another alternative embodiment which is very similar to that depicted in FIG. 9. Accordingly, like numerals in FIG. 12 indicate the same elements as defined in connection with FIG. 9. In the embodiment of FIG. 12, the base end 380 of the body 310 is planar and defines the aperture 382. As a result of this configuration, the base end 380 does not complement the geometry of the syringe or the needle assembly. When the needle 232 passes through the aperture 282, the the conical portion 234 will abut the end 380. Since this configuration results in a foreshortened closed end, it is desirable to retract the needle further into the body 3 10. In order to accomplish this further retraction, the resilient compressive member 400 is enlarged. In this embodiment, the compressive resilient element has three rings 402, 406 and 410 which alternate with the circular reliefs 404 and 408. Like the prior embodiment, the resilient compressive member 400 includes a conical portion 412 which defines the central aperture 414. As with the prior configuration, the central aperture 414 is dimensioned to have an interference fit with the conical portion 234 of needle assembly 230.

As can be seen from a comparison of FIGS. 9 and 12, the resilient compressive element will be sized to provide a retractive force sufficient to retract the needle 232 behind the base end 380.

Figure 13:
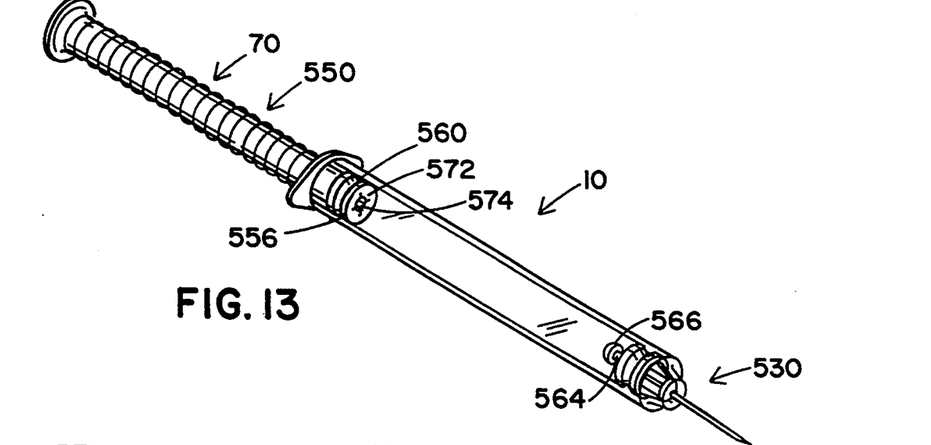
FIG. 13 depicts an alternative arrangement of the ball and socket embodiment of the present invention.
Figure 14:
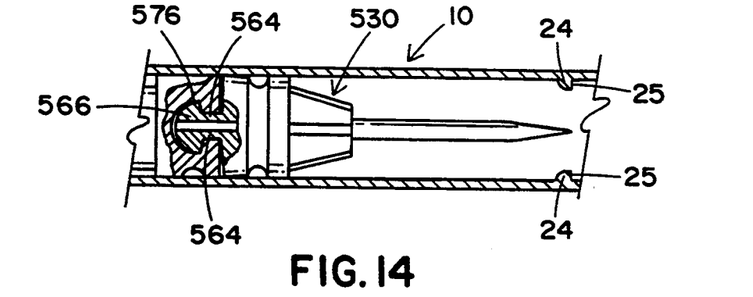
FIG. 14 is an exploded view of the ball and socket interconnection of the embodiment depicted in FIG. 13.

An alternative arrangement of the ball and socket configuration of the first embodiment is depicted in FIGS. 13 and 14. With respect to FIG. 13, the syringe is identical to that previously described in connection with FIG. 1 and the compress ire member 70 is identical to the compressive member of FIG. 1. The plunger 550 is similar to that described with respect to FIG. 1 except that the sealing member 556 differs from that of the prior embodiment. In the present embodiment, the sealing member 556 includes a forward portion 572 which includes a scored area 574, which is disposed forward of the hemispheric recess 560. Beneath the sealing member 556 is the recess 576, see FIG. 14, which is dimensioned to accept the hemisphere 566 and shaft 564 of the needle assembly 530. In this embodiment, the recess 576 is closed by the sealing member 556 until such time as the scored area 574 come into contact with the hemisphere 566. As continued pressure is applied, the scored area 574 yields to the hemisphere 566 and the male member becomes inserted into the recess 576. With reference to FIG. 14, the hemisphere 566 is supported by a plurality of columns 564 which stand off from the needle assembly to permit fluid to pass beneath the projection 566 and through the needle. The recess 576 is dimensioned so as to allow travel of the plunger into full contact with needle assembly 530. As in the prior embodiments, the needle assembly is retained by the projections 24.

Figure 15:
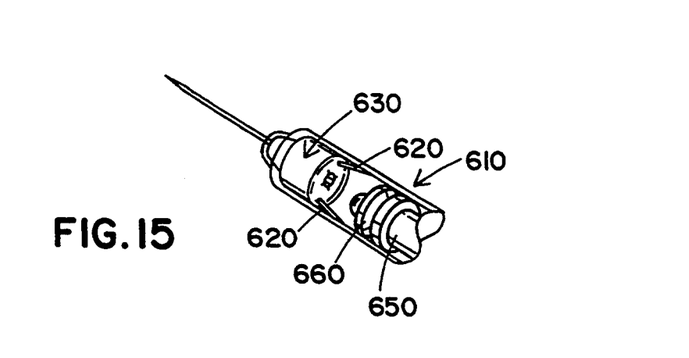
FIG. 15 depicts an alternative embodiment of the needle assembly which incorporates a compressive spring member therein.
Figure 16:
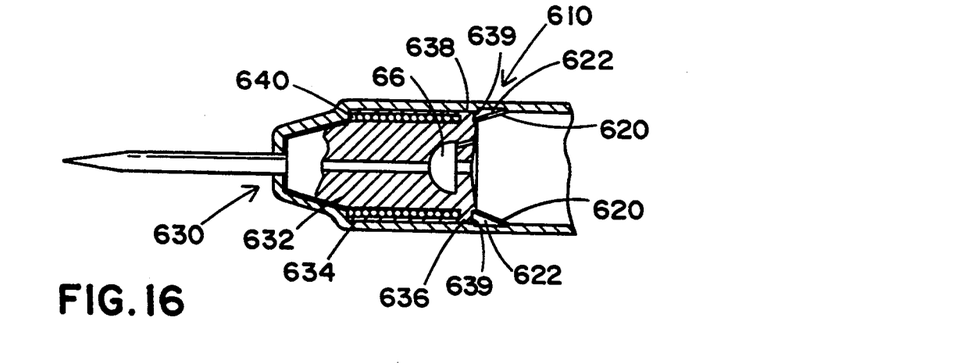
FIG. 16 depicts an exploded view of the embodiment of FIG. 15.

A further alternative embodiment of the present invention will be described with reference to FIGS. 15 and 16. In FIG. 15, there is depicted a syringe 610 in which the needle assembly 630 is retained in the syringe by the hinged, finger like projections 620, see FIG. 16. The plunger 650 includes a forward sealing member 660 which collapses the fingers 620 against the wall of the syringe 610 as the plunger is moved toward the needle during injection. With reference to FIG. 16, this embodiment will be described in more detail. The needle assembly 630 is similar to assembly 30 which has been previously described. However, in this embodiment the needle assembly has a body portion 632 and a skirt portion 636 which defines the recess 634 in which the compressive member 640 is seated. As in prior embodiments, a sealing ring 638 is provided. The sealing ring 638 includes the depressed portions 639 which abut the finger like projections 620. In this embodiment, the compress ire spring member 640 is contained within the recess 634 in a fully compressed state. The spring remains under compression as a result of the fingers 620 holding the assembly 630 in the syringe body 610. When an injection has been completed, the sealing member 660 will depress the hinged fingers 620 into the recesses 622. In this embodiment, the socket 66 is provided so that there is a locking contact between the plunger and the needle assembly. When pressure is released from the plunger, the spring 640 will be decompressed. As a result of the skirt 634, the needle assembly will pass the fingers 620 without interference between the spring 640 and the fingers 620. While it is preferred to provide a positive locking between the plunger and the needle assembly as shown in this embodiment, the positive locking may be dispensed with by modifying the depressed portions 639 to be an angled, ramp like configuration which will easily slide beyond the fingers 620.

With respect to the compressive members 70, 330, 400 and 640, it will be appreciated that the specific configurations are by way of example and not by way of limitation. However, it is essential that the compressive member has sufficient force to retract the needle into the protective cover.

I claim:

1. A syringe (10) having a one piece hollow body (12) that is open at a first end (14) and is substantially closed at the other end (18) except for an aperture (22) through which an injection means (32) passes and a plunger (50), which has a geometrically configured portion (66), that moves in the hollow body (12) toward the substantially closed end (18), the syringe (10) is characterized by:

a needle assembly (30) that is positioned in the hollow body (12) adjacent to the substantially closed end (18) and in sealing engagement with the hollow body, the assembly has a body portion (34, 36, 38, 40) unified with the injection means (32), the body portion has an injection means side and a plunger side with a central passage that extends between the sides and forms a communication path (47) between the hollow body (12) and the injection means (32), the plunger side of the body portion has a geometrically configured cavity (46) that mates with the geometrically configured portion (66) of the plunger (50) and locks the plunger and the needle assembly together as a single unit.

2. The syringe of claim 1 wherein the hollow body has at least one interior projection positioned adjacent to the closed end of the hollow body.

3. The syringe of claim 2 wherein the body portion of the needle assembly has an annular recess that receives and complements the projection.

4. The syringe of claim 2 wherein the body portion of the needle assembly has a collar which is positioned between the projection and the closed end of the hollow body and secures the needle assembly in the closed end.

5. The syringe of claim 1 wherein the body portion of the needle assembly has a sealing ring which establishes a liquid tight seal against the interior of the hollow body.

6. The syringe of claim 1 wherein the body is further characterized by a conical recess that tapers towards the central passage and opens into the cavity via a central aperture.

7. The syringe of claim 6 wherein a plurality of tubes extend between the conical recess and the cavity.

8. The syringe of claim 6 wherein the cavity communicates with a central tube which is in communication with the injection means.

9. The syringe of claim 1 wherein the body portion of the needle assembly is formed as a unitary molding of synthetic material.

10. The syringe of claim 9 wherein the hollow body has at least one interior projection positioned adjacent to the closed end of the hollow body.

11. The syringe of claim 10 wherein the body portion of the needle assembly has a sealing ring which establishes a liquid tight seal against the interior of the hollow body.

12. The syringe of claim 11 wherein the geometrically configured cavity locks with the geometrically configured portion of the plunger and withdraw of the plunger toward the open end deforms the body portion so that the needle assembly traverses the projection and moves in unison with the plunger.

13. The syringe of claim 1 further characterized by a resilient member which urges the plunger away from the closed end.

14. A syringe having a one piece hollow body that is open at a first end and is substantially closed at the other end except for an aperture through which an injection means passes, a plunger having a geometrically configured portion, that moves in the hollow body toward the substantially closed end, and a needle assembly, having a geometrically configured cavity that mates with the geometrically configured portion of the plunger and locks the plunger and the needle assembly together as a single unit and an injection means, the syringe is characterized by:

a needle assembly, having a body portion unified with the injection means, the body portion has an injection means side and a plunger side with a central passage that extends between the sides and forms a communication path between the hollow body and the injection means, the needle assembly is positioned in the hollow body adjacent to and in sealing engagement with the substantially closed end and only injection means passes through the aperture.

15. A syringe having a hollow body, which is open at a first end and is closed at the other end except for an aperture through which an injection means passes, and a plunger, which has a geometrically configured portion that moves in the hollow body toward the closed end, the syringe is characterized by:

a unified needle assembly, comprised of a body portion and the injection means, that is positioned in the hollow body adjacent to the closed end with only the injection means passing through the aperture; the body portion has a sealing member which seals against the interior of the hollow body, the body portion is the only sealing element between the plunger and the aperture through the closed end and includes a geometrically configured cavity that mates with the geometrically configured portion of the plunger to lock the plunger and the unified needle assembly together as a single unit.

16. A syringe of a type having an elongated, hollow body and a plunger which moves within the hollow body, the body has an open first end and a substantially closed second end that defines an aperture through which an injection means passes, the plunger has a geometrically configured portion that moves in the hollow body from the open end toward the substantially closed second end, the syringe is characterized by:

a unified needle assembly that is comprised of a body portion and the injection means; the body portion of the needle assembly is positioned in the hollow body between the plunger and the substantially closed second end and includes a sealing means which seals against the interior of the hollow body, the body portion of the needle assembly is the only sealing means in the hollow body between the plunger and the aperture and only the injection means passes through the aperture.

17. A disposable, single use syringe comprised of:

a generally elongated hollow body that is open at a first end and substantially closed at a second end to define a body closure having an injection needle aperture therein, the hollow body has a substantially uniform interior diameter between the first end and a needle assembly retaining means that is positioned adjacent to the closed end;

a plunger which moves within the hollow body between the first end and the closed end, the plunger includes a sealing means which seals against the interior of the hollow body; and a unified needle assembly which is located in the hollow body adjacent to the closed end, the assembly includes a deformably body portion and the injection needle, the body portion has forward and rearward ends, the injection needle, which passes through the aperture in the second end of the elongated hollow body, has a predetermined length with free and fixed ends and an exterior diameter which is no greater than the diameter of the aperture, the fixed end of the injection needle is foxed in the forward end of the body portion, the body portion is located wholly within the hollow body and is configured to substantially compliment the closed end of the elongated hollow body, the rearward end of the body portion compliments the interior diameter of the elongated hollow body and seals against the interior of the hollow body, the rearward end of the body portion further includes a position retaining means which cooperates with the needle assembly retaining means to releasably retain the needle assembly location in the hollow body, whereby the cooperation between the position retaining means and the needle assembly retaining means is overcome by application of a force to the needle assembly, directed toward the first end of the hollow body, that causes deformation of the deformably body.

18. A syringe having a one piece hollow body of constant interior diameter between a first end, which is open and has an interior diameter at least as great as the interior diameter of the hollow body, and a second end, which is substantially closed except for a central aperture, and a plunger, which has a sealing end that passes through the open end and seals against the interior of the hollow body and a geometrically configured portion forward of the sealing end, that moves in the hollow body towards the substantially closed end, characterized by:

a needle assembly, comprised of unified body and injection needle portions, positioned in the hollow body adjacent to the second end with only the injection needle portion passing through the central aperture; the body portion has an injection needle side and a plunger side, the exterior of the body portion seals the hollow body at the substantially closed end and the interior of the body portion defines a communication path between the hollow body and the injection needle, the plunger side of the body portion has a second geometrically configured portion that receives the geometrically configured portion of the plunger and locks the plunger and needle assembly together whereby movement of the locked plunger and needle assembly towards the open end draws the injection needle through the aperture and the entire needle assembly into the hollow body.

* * * * *